US012796966B2

(12) United States Patent
Zhu et al.

(10) Patent No.: US 12,796,966 B2
(45) Date of Patent: Nov. 17, 2026

(54) METHOD AND SYSTEM FOR PROCESSING GAIT DATA

(71) Applicant: Shenzhen Shokz Co., Ltd., Shenzhen (CN)

(72) Inventors: Huijin Zhu, Shenzhen (CN); Lei Su, Shenzhen (CN); Xin Zhou, Shenzhen (CN); Meiqi Li, Shenzhen (CN); Fengyun Liao, Shenzhen (CN); Xin Qi, Shenzhen (CN)

(73) Assignee: Shenzhen Shokz Co., Ltd., Shenzhen (CN)

( * ) Notice: Subject to any disclaimer, the term of this patent is extended or adjusted under 35 U.S.C. 154(b) by 231 days.

(21) Appl. No.: 18/744,476

(22) Filed: Jun. 14, 2024

(65) Prior Publication Data

US 2024/0335139 A1 Oct. 10, 2024

Related U.S. Application Data

(63) Continuation of application No. PCT/CN2023/087101, filed on Apr. 7, 2023.

(51) Int. Cl.
*A61B 5/11* (2006.01)
*A61B 5/00* (2006.01)

(52) U.S. Cl.
CPC ............ *A61B 5/112* (2013.01); *A61B 5/0004* (2013.01); *A61B 5/6829* (2013.01); *A61B 5/7282* (2013.01); *A61B 2562/0219* (2013.01)

(58) Field of Classification Search
CPC ..... A61B 5/112; A61B 5/0004; A61B 5/6829; A61B 5/7282; A61B 2562/0219
See application file for complete search history.

(56) References Cited

U.S. PATENT DOCUMENTS 6,876,947 B1 * 4/2005 Darley .................... G01P 1/023 702/144
2020/0305764 A1 10/2020 Aibara
2021/0001176 A1 * 1/2021 Weast .................. A61B 5/7257

FOREIGN PATENT DOCUMENTS

CN 104436597 A 3/2015
CN 112263246 A 1/2021
(Continued)

OTHER PUBLICATIONS

Wang, Wenjian, et al. "Gait Phase Discrimination Based on a Foot-Mounted Gyroscope." 2019 12th International Congress on Image and Signal Processing, BioMedical Engineering and Informatics (CISP-BMEI). IEEE, 2019. (Year: 2019).*
(Continued)

*Primary Examiner* — Eric J Messersmith
(74) *Attorney, Agent, or Firm* — Fideli Law PLLC; Qiang Li

(57) ABSTRACT

A method and system for processing gait data includes: obtaining gait data for M gait cycles of the target user's lower limbs, and determining, based on the gait data, the target lift-off moment when the target user's foot leaves the ground for each of the M gait cycles. Subsequently, gait features of the target user are determined based on at least the target lift-off moments corresponding to each of the M gait cycles. The value of the sliding factor is dynamically updated for each gait cycle to obtain the target sliding factor value. The target sliding factor value is associated with the user's motion state in that gait cycle. The lift-off time range is determined in the current gait cycle, and the target lift-off moment is determined in that gait cycle based on the target sliding factor value and the lift-off time range.

18 Claims, 7 Drawing Sheets

(56) References Cited

FOREIGN PATENT DOCUMENTS

| | | | |
|---|---|---|---|
| CN | 113180644 | A | 7/2021 |
| CN | 113303789 | A | 8/2021 |
| CN | 115357119 | A | 11/2022 |
| CN | 119110705 | A | 12/2024 |
| WO | 2014043757 | A | 3/2014 |
| WO | 2014043757 | A1 | 3/2014 |
| WO | 2022066093 | A | 3/2022 |

OTHER PUBLICATIONS

International Search Report for PCT/CN2023/087101 (Jan. 5, 2024).

Written opinion of the International Searching Authority for PCT/CN2023/087101 (Jan. 5, 2024).

* cited by examiner

METHOD AND SYSTEM FOR PROCESSING GAIT DATA

RELATED APPLICATIONS

This application is a continuation application of PCT application No. PCT/CN2023/087101, filed on Apr. 7, 2023, and the content of which is incorporated herein by reference in its entirety.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

TECHNICAL FIELD

This disclosure relates to the field of data processing technology, particularly relates to a method and system for processing gait data.

BACKGROUND

Gait analysis finds widespread applications in various fields. For instance, in the realm of running, it can guide users in correcting their running posture based on the analysis results. Similarly, in the field of rehabilitation assessment, the results of gait analysis can be used to evaluate the physical rehabilitation progress of users.

The typical process of gait analysis involves several steps: pre-defining specific gait events, taking running as an example, landing of the heel can be defined as a ground contact event, while lifting of the toe can be defined as a lift-off event. Subsequently, based on the collected gait data, the occurrence times of these gait events are determined, and the user's gait characteristics are analyzed based on these event occurrences. It's evident that accurately determining the occurrence times of gait events is a crucial step in gait analysis. When there's significant error in determining the occurrence times of gait events, the results of gait analysis can also be inaccurate. Therefore, there's a need to provide a gait data processing method capable of accurately determining the occurrence times of gait events.

SUMMARY

The present disclosure provides a method and system for processing gait data in order to accurately determine the occurrence times of gait events, thereby ensuring a high level of accuracy in gait analysis results.

In a first aspect, the present disclosure provides a system for gait data processing, including: at least one storage medium storing at least one set of instructions for gait data processing; and at least one processor in communication with the at least one storage medium, where during operation, the at least one processor executes the at least one set of instructions to cause the system to at least: obtain gait data of M gait cycles of a lower limb of a target user, where M is an integer greater than 1; respectively determine, based on the gait data, target lift-off moments when a feet of the target user leaves the ground in the M gait cycles, where a gait cycle corresponding to currently processed gait data is a gait cycle, and a process for determining a target lift-off moment corresponding to the target gait cycle includes: dynamically updating a sliding factor value according to the target gait cycle to obtain a target sliding factor value, where the target sliding factor value is related to a user motion state in the target gait cycle, and determining a lift-off time range in the target gait cycle and determining the target lift-off moment based on the target sliding factor value and the lift-off time range; and determine a gait feature of the target user based on at least the target lift-off moments corresponding to the M gait cycles.

In a second aspect, the present disclosure provides a method for gait data processing, including: obtaining gait data of M gait cycles of a lower limb of a target user, where M is an integer greater than 1; respectively determining, based on the gait data, target lift-off moments when a feet of the target user leaves the ground in the M gait cycles, where a gait cycle corresponding to currently processed gait data is a gait cycle, and a process for determining a target lift-off moment corresponding to the target gait cycle includes: dynamically updating a sliding factor value according to the target gait cycle to obtain a target sliding factor value, where the target sliding factor value is related to a user motion state in the target gait cycle, and determining a lift-off time range in the target gait cycle and determining the target lift-off moment based on the target sliding factor value and the lift-off time range; and determining a gait feature of the target user based on at least the target lift-off moments corresponding to the M gait cycles.

From the above technical solutions, it is evident that the method and system for processing gait data provided by the present disclosure can obtain gait data for M gait cycles of a target user's lower limbs. Based on the gait data, it determines the target lift-off times when the user's foot leaves the ground for each of the M gait cycles. Subsequently, it determines the gait characteristics of the target user based on the target lift-off times corresponding to each of the M gait cycles. During the processing of gait data, the system dynamically updates the value of the sliding factor for each gait cycle to obtain a target sliding factor value. This target sliding factor value is related to the user's movement state in that gait cycle. Consequently, the system determines the lift-off time range in the current gait cycle and, based on the target sliding factor value and the lift-off time range, determines the target lift-off time in that gait cycle. Since the value of the sliding factor is dynamically updated in real-time according to the user's movement state in the current gait cycle, the target lift-off time determined based on the target sliding factor value is more accurate. Consequently, the gait characteristics determined based on the target lift-off time are also more accurate. Therefore, the gait analysis results exhibit a higher level of accuracy.

The present disclosure provides additional functionalities of the method and system for processing gait data, some of which will be outlined in the following description. The inventive aspects of the method and system provided by the present disclosure can be fully understood through practice or utilization of the methods, devices, and combinations described in detail in the following examples.

BRIEF DESCRIPTION OF THE DRAWINGS

In order to clearly illustrate the technical solutions of the embodiments of the present disclosure, the following will briefly introduce the drawings for the description of some exemplary embodiments. Apparently, the accompanying drawings in the following description are some exemplary embodiments of the present disclosure. For a person of ordinary skill in the art, other drawings may also be obtained based on these drawings without creative efforts.

DETAILED DESCRIPTION

Figure 1:
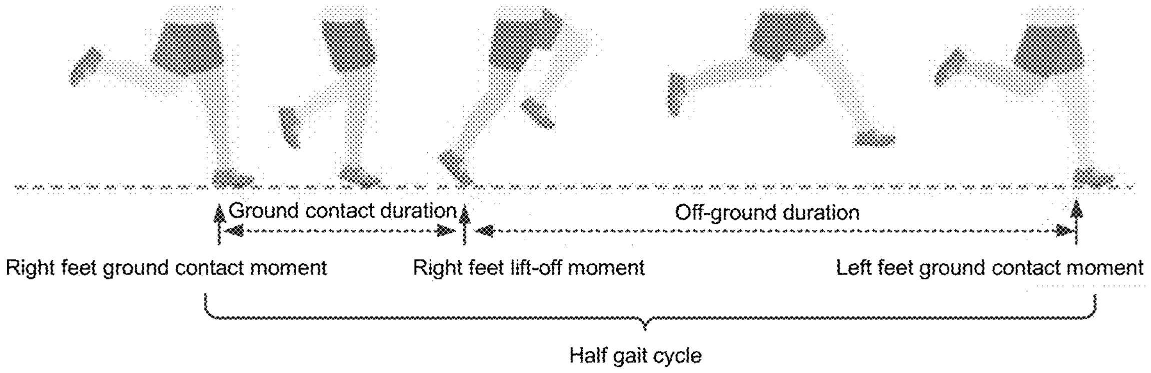
FIG. 1 is a schematic diagram of a user's running process according to some exemplary embodiments of the present disclosure.

The following description provides specific application scenarios and requirements of the present disclosure, with the aim of enabling a person skilled in the art to manufacture and utilize the content of the present disclosure. For a person skilled in the art, it is evident that various partial modifications to the disclosed embodiments are feasible, and the general principles defined herein can be applied to other embodiments and applications without departing from the spirit and scope of the present disclosure. Therefore, the present disclosure is not limited to the embodiments shown herein but encompasses the broadest scope consistent with the claims.

The terms used here are merely for the purpose of describing specific exemplary implementations, and are not restrictive. For example, unless otherwise specified in context, the singular forms "a," "an", and "the" may also include plural forms. When used in the present disclosure, the terms "comprising," "including," and/or "having" mean that the associated integers, steps, operations, elements, and/or components are present, but do not exclude the presence of one or more other features, integers, steps, operations, elements, components, and/or groups thereof, or that additional features, integers, steps, operations, elements, components, and/or groups may be added in the system/method.

Considering the following description, the features of the present disclosure, along with other features, as well as the operations and functionalities of the relevant components of the structure, and the combination and economical manufacturing of parts, can be significantly improved. Reference is made to the drawings, all of which form part of the present disclosure. However, it should be understood that the drawings are for illustrative and descriptive purposes only, and are not intended to limit the scope of the present disclosure. It should also be understood that the drawings are not drawn to scale.

The flowchart used in the present disclosure illustrates the operations of the system implementation according to some embodiments of the present disclosure. It should be understood that the operations in the flowchart may not be implemented sequentially. Instead, operations may be implemented in reverse order or simultaneously. Additionally, one or more additional operations can be added to the flowchart, and one or more operations can be removed from the flowchart.

For ease of description, the terms used in the present disclosure will be explained firstly.

Gait refers to the posture and behavioral characteristics of a person's walking or running. Specifically, gait refers to the series of continuous movements of the hip, knee, ankle, and toes that enable the body to move in a certain direction. Gait is a continuous, cyclical movement influenced by factors such as habitual movements, disabilities, and illnesses, resulting in generally unique gaits for different individuals.

Gait analysis refers to the method of studying the patterns of walking, which can describe the characteristics of gait with various parameters. These parameters typically include the following categories: gait cycle, kinematic parameters, kinetic parameters, electromyographic activity parameters, and energy metabolism parameters, among others. The results of gait analysis can be used to guide users in correcting their movement posture, as well as for rehabilitation assessment, clinical diagnosis, and mechanistic research, among other purposes.

Taking the running scene as an example, FIG. 1 shows a schematic diagram of a user's running process according to some exemplary embodiments of the present disclosure. The following explains the gait events, ground contact duration, lift-off duration, and gait cycle in conjunction with FIG. 1.

The gait events refer to events used to describe the motion state of the human body during walking or running. Usually, to facilitate gait analysis, some gait events can be predefined. Common gait events include but are not limited to: ground contact events and lift-off events. For example, referring to FIG. 1, the ground contact event refers to when a user's foot begins to contact the ground. It should be understood that during a running process, the process of the foot contacting the ground is usually the heel first and then the toes, so the "foot beginning to contact the ground" mentioned above can specifically refer to the heel beginning to contact the ground. The moment of the ground contact event refers to the moment when the user's foot begins to contact the ground (also known as ground contact moment for short). The ground contact event can be specifically divided into left foot ground contact event and right foot ground contact event. The lift-off event refers to when a user's foot leaves the ground. In a running process, the process of the foot leaving the ground is usually the heel leaving the ground first and then the toes, so the "foot leaving the ground" mentioned above can specifically refer to the user's toes leaving the ground. The moment of lift-off event refers to the moment when the user's foot leaves the ground (also known as lift-off moment for short). The lift-off event can be specifically divided into left foot lift-off event and right foot lift-off event.

Ground contact duration: during a process of walking or running, the time interval between the initial contact of the foot on one side of the user (corresponding to the ground contact event) and the lift-off of that side's foot (corresponding to the lift-off event) is referred to as the ground contact duration. The ground contact duration represents the entire time taken by the foot of one side to perform the processes of landing, supporting, pushing off, and lift-off, for example, referring to FIG. 1, taking a user's right foot as an example, subtracting the time of the most recent right foot lift-off from the time of the most recent right foot ground contact yields the ground contact duration of the right foot. The ground contact duration can be used to analyze running efficiency. For instance, a shorter ground contact duration indicates a higher efficiency in the conversion of muscle elastic energy, thus resulting in higher running efficiency. The ground contact duration for proficient runners typically falls in 220 milliseconds or less. Additionally, the ground contact duration for each foot can be used to analyze gait balance. For example, the smaller the difference in ground contact duration between the corresponding feet, the higher the gait balance; conversely, the greater the difference in ground contact duration between the corresponding feet, the lower the gait balance.

Off-ground duration: during a process of walking or running, the time interval between the lift-off of one foot on one side of a user (corresponding to the lift-off event) and the initial ground contact of the other foot on the opposite side (corresponding to the ground contact event) is referred to as the off-ground duration. The off-ground duration represents the duration in which both feet are simultaneously off the ground. For example, referring to FIG. 1, subtracting the time of the most recent lift-off of the right foot from the time of the most recent ground contact of the left foot gives the off-ground duration after the lift-off of the right foot. In gait analysis, the off-ground duration can be used to analyze running efficiency. For instance, at the same step frequency, a longer off-ground duration indicates a larger stride, hence higher running efficiency. The off-ground duration for proficient runners typically exceeds 125 milliseconds.

Gait cycle: during a process of walking or running, the time interval between the initial contact of one foot on one side of a user with the ground (corresponding to the ground contact event) and the subsequent contact of the same foot with the ground on that side (corresponding to the ground contact event) is referred to as one gait cycle. For example, referring to FIG. 1, a complete gait cycle can refer to the duration from the right foot's ground contact moment to the next right foot's ground contact moment, which corresponds to the sum of the following four durations: the right foot's ground contact duration, the off-ground duration after the lift-off of the right foot, the left foot's ground contact duration, and the off-ground duration after the lift-off of the left foot. It should be understood that FIG. 1 only illustrates half of a gait cycle.

The processing method and system for gait data provided by the present disclosure can be applied in gait analysis scenarios. For example, during a user's walking or running, sensors worn in the range of the user's lower limbs collect gait data. A processor then utilizes the processing method for gait data provided by the present disclosure to analyze the collected gait data and determine the user's gait characteristics. These gait characteristics can be used to correct the user's movement posture.

It should be noted that the walking or running scenario mentioned above is just one of many usage scenarios provided by the present disclosure. The solutions provided by the present disclosure can not only be applied in walking or running scenarios but also in all other scenarios that require gait analysis, such as rehabilitation assessment, sports biomechanics research, and so on. A person skilled in the art could understand that the application of the solutions provided by the present disclosure in other usage scenarios is also in the scope of protection of the present disclosure.

The solution provided in the present disclosure, when processing gait data, can dynamically update the value of the sliding factor for each gait cycle to obtain the target sliding factor value. This target sliding factor value is related to a user's motion state in the gait cycle. Consequently, it determines the lift-off time range in the current gait cycle and, based on the target sliding factor value and the lift-off time range, determines the target lift-off moment in that gait cycle. Since the value of the sliding factor is dynamically updated in real-time based on the user's motion state in the current gait cycle, the target lift-off moment determined based on the target sliding factor value is more accurate. Consequently, the gait features determined based on the target lift-off moment are also more accurate. Therefore, the gait analysis results have a higher level of accuracy.

Figure 2:
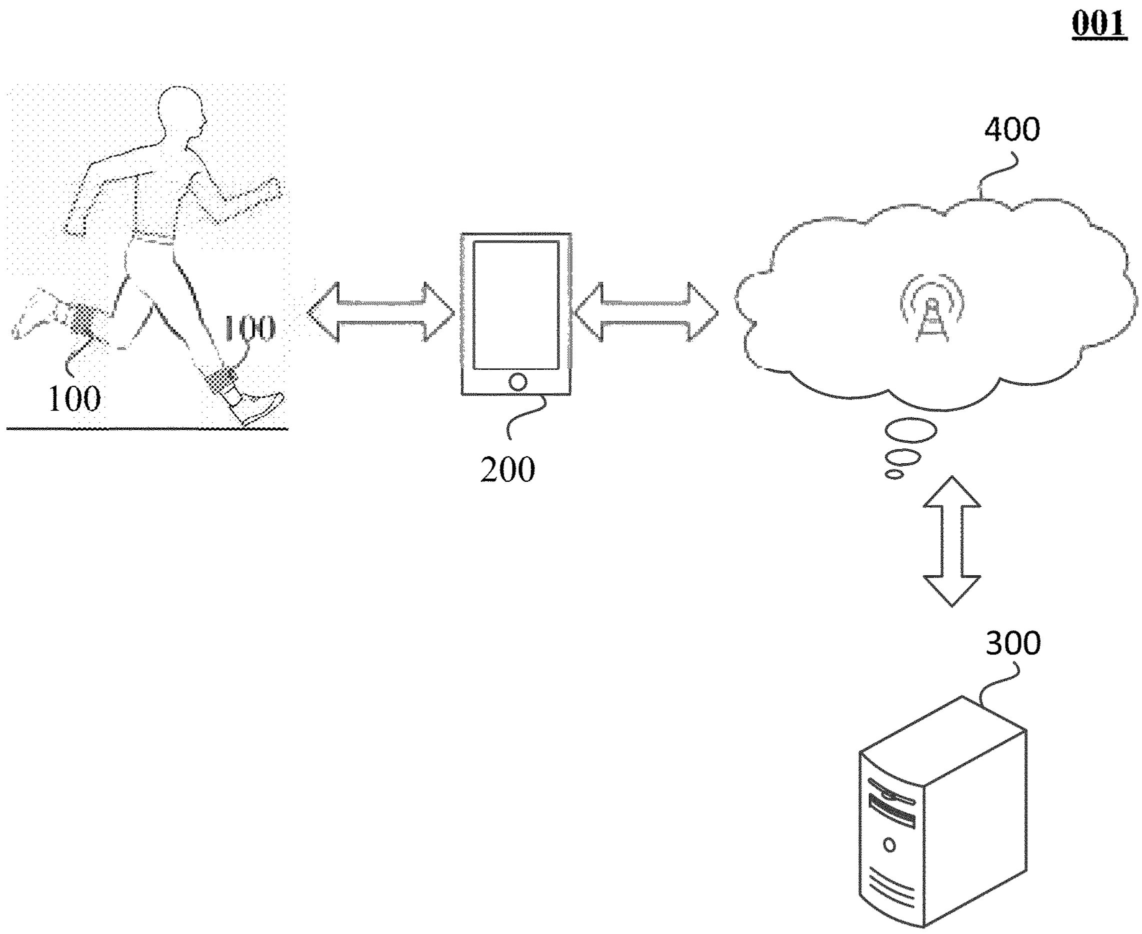
FIG. 2 is a schematic diagram of a system for processing gait data according to some exemplary embodiments of the present disclosure.

FIG. 2 is a schematic diagram of a system for processing gait data according to some exemplary embodiments of the present disclosure. The gait data processing system 001 (hereinafter referred to as the system 001) can be used for all scenarios of gait analysis. As shown in FIG. 2, in some exemplary embodiments, the system 001 may include a wearable device 100. In some exemplary embodiments, the system 001 may include the wearable device 100 and a control device 200. In some exemplary embodiments, the system 001 may include the wearable device 100, the control device 200, a server 300, and a network 400.

The wearable device 100 refers to a portable device that can be worn on a user's body, shoes, clothing, or other accessories. The wearable device 100 is designed to be worn on the lower limbs of the user. As shown in FIG. 1, the wearable device 100 can be worn on the user's left leg to collect gait data corresponding to the left leg during operation. It can also be worn on the user's right leg to collect gait data corresponding to the right leg. Additionally, the wearable device 100 can be worn on both the left and right legs simultaneously to collect gait data for both legs. In some exemplary embodiments, the wearable device 100 can be worn on the user's ankle. Since the ankle is closer to the foot, gait data from the ankle can more accurately reflect the user's gait features.

The wearable device 100 can include sensors for collecting gait data. These sensors may include one or more of the following: accelerometer sensors, gyroscope sensors, and inertial sensors, etc.

The accelerometer sensor is capable of measuring acceleration, sensing it during operation, and converting it into usable output signals. Typically, an accelerometer sensor contains a mass block. Its principle of measuring acceleration is as follows: during acceleration, the sensor measures the inertial force acting on the mass block and applies Newton's second law to obtain the acceleration value. Accelerometer sensors can be of various types, including capacitive sensors, inductive sensors, strain sensors, piezoresistive sensors, or any combination thereof. In some exemplary embodiments, the accelerometer sensor can be a 3-axis accelerometer, measuring acceleration data along the X, Y, and Z axes in space coordinates. This allows for a more comprehensive reflection of the object's motion characteristics.

The angular velocity sensor, also known as a gyroscope, is a sensor capable of measuring angular velocity. It senses changes in angular velocity during operation and converts them into usable output signals. Gyroscope sensors can be single-axis (measuring angular velocity along a single direction) or multi-axis (such as three-axis sensors, measuring the rotation of an object around the X, Y, and Z axes).

The inertial sensor, also known as an Inertial Measurement Unit (IMU), can be understood as a sensor that integrates both accelerometer and gyroscope functionalities. In other words, an inertial sensor can sense changes in both acceleration and angular velocity during operation, thereby outputting corresponding signals for both acceleration and angular velocity.

In summary, the solutions presented in the present disclosure involve deploying sensors in wearable device 100 to collect gait data. Compared to specialized equipment such as force sensing treadmills or force plates, this approach offers several advantages. On the one hand, it is cost-effective and relatively inexpensive. On the other hand, it is flexible in terms of application scenarios, as it can be used both indoors and outdoors.

In some exemplary embodiments, the gait data processing method described in the present disclosure can be executed by the wearable device 100. In this scenario, the wearable device 100 can store data or instructions for executing the gait data processing method described in the present disclosure, and it can execute or be used to execute such data or instructions. In some exemplary embodiments, the wearable device 100 may include hardware devices with data processing capabilities and the programs required to drive the operation of these hardware devices. The details of the gait data processing method will be described in other parts of the present disclosure.

The control device 200 can include mobile devices, tablets, laptops, onboard devices in vehicles, or similar equipment, or any combination thereof. In some exemplary embodiments, the mobile device may include smart home devices, smart mobile devices, virtual reality devices, augmented reality devices, or similar devices, or any combination thereof. In some exemplary embodiments, the smart home devices may include smart TVs, desktop computers, or any combination thereof. In some exemplary embodiments, the smart mobile devices may include smartphones, personal digital assistants, gaming devices, navigation devices, or any combination thereof. In some exemplary embodiments, the virtual reality devices or augmented reality devices may include virtual reality headsets, virtual reality glasses, augmented reality headsets, augmented reality glasses, or similar equipment, or any combination thereof. For example, the virtual reality devices or augmented reality devices may include Google Glass, head-mounted displays, VR, etc. In some exemplary embodiments, the onboard devices in vehicles may include onboard computers, car TVs, and so on.

As shown in FIG. 2, the control device 200 can be connected to the wearable device 100 for communication. The control device 200 and the wearable device 100 can be connected via wired means, such as through Universal Serial Bus (USB) connection or other wired methods. The control device 200 can also be connected to the wearable device 100 via short-range wireless means, such as Bluetooth connection, Near Field Communication (NFC) connection, Wi-Fi connection, or other wireless methods. In some exemplary embodiments, the control device 200 and the wearable device 100 can also be connected via the network 400, where both the control device 200 and the wearable device 100 are connected to the network 400. In some exemplary embodiments, information exchange can occur between the wearable device 100 and the control device 200. For instance, after collecting gait data, the wearable device 100 can send the gait data to the control device 200. In some exemplary embodiments, the gait data processing method described in the present disclosure can be executed on/by the control device 200. In this case, the control device 200 can store data or instructions for executing the gait data processing method described in the present disclosure, and it can execute or be used to execute such data or instructions. In some exemplary embodiments, the control device 200 may include hardware devices with data processing capabilities and the programs required to drive the operation of these hardware devices. The details of the gait data processing method will be described in other parts of the present disclosure.

In some exemplary embodiments, the control device 200 can be equipped with one or more applications (apps) that provide interactive interfaces for users. These apps may include, but are not limited to: web browsers, search engines, messaging apps, shopping apps, video apps, finance management tools, instant messaging tools, email clients, social media platforms, health management tools, exercise management tools, and so on. In some exemplary embodiments, the control device 200 may have specific apps installed. Users can use these apps to trigger requests for gait data collection. The designated app can respond to such requests by sending control commands to the wearable device 100, instructing it to start collecting gait data. In some embodiments, users can also trigger requests for gait data processing through the designated app. The designated app can respond to such processing requests by executing the gait data processing method described in the present disclosure to obtain the user's gait features. Additionally, in some exemplary embodiments, the designated app can present the user's gait features to the user through voice or visual means.

The server 300 can be a server that provides various services, such as providing computing and/or storage services to the control device 200 as a backend server. As shown in FIG. 2, the server 300 can communicate with one or more control devices 200 and exchange information between them. For example, the control device 200 can send raw gait data to the server 300 for processing, and the server 300 can send back the processed gait features to the control device 200. In some exemplary embodiments, the method for processing the gait data described in the present disclosure can be performed on the server 300. In this case, the server 300 can store data or instructions for performing the method described in the present disclosure and execute or use the data or instructions for execution. In some exemplary embodiments, the server 300 may include hardware devices with data processing capabilities and programs necessary to drive the hardware devices. The method for processing gait data will be described in other parts of the present disclosure.

The network 400 can be used to provide communication connections between the control device 200 and the server 300. The network 400 facilitates the exchange of information or data. As shown in FIG. 2, the control device 200 and the server 300 can be connected to the network 400 and exchange information or data with each other via the network 400. In some exemplary embodiments, the network 400 can be any type of wired or wireless network, or a combination thereof. For example, the network 400 can include cable networks, wired networks, fiber optic networks, telecommunications networks, intranets, the internet, local area networks (LANs), wide area networks (WANs), wireless LANs (WLANs), metropolitan area networks (MANs), public switched telephone networks (PSTNs), Bluetooth networks, ZigBee networks, near-field communication (NFC) networks, and the like. In some exemplary embodiments, the network 400 may include one or more network access points. For example, the network 400 can include wired or wireless network access points, such as base stations or internet exchange points, through which one or more components of the control device 200 and the server 300 can connect to the network 400 to exchange data or information.

It should be understood that the number of wearable devices 100, control devices 200, servers 300 and networks 400 depicted in FIG. 1 is purely illustrative. Depending on the implementation requirements, any number of wearable devices 100, control devices 200, servers 300 and networks 400 can be employed.

It is worth noting that the method for processing gait data described in the present disclosure can be entirely executed on the wearable device 100, entirely on the control device 200, entirely on the server 300, or jointly by at least two of the wearable device 100, control device 200 and server 300.

Figure 3:
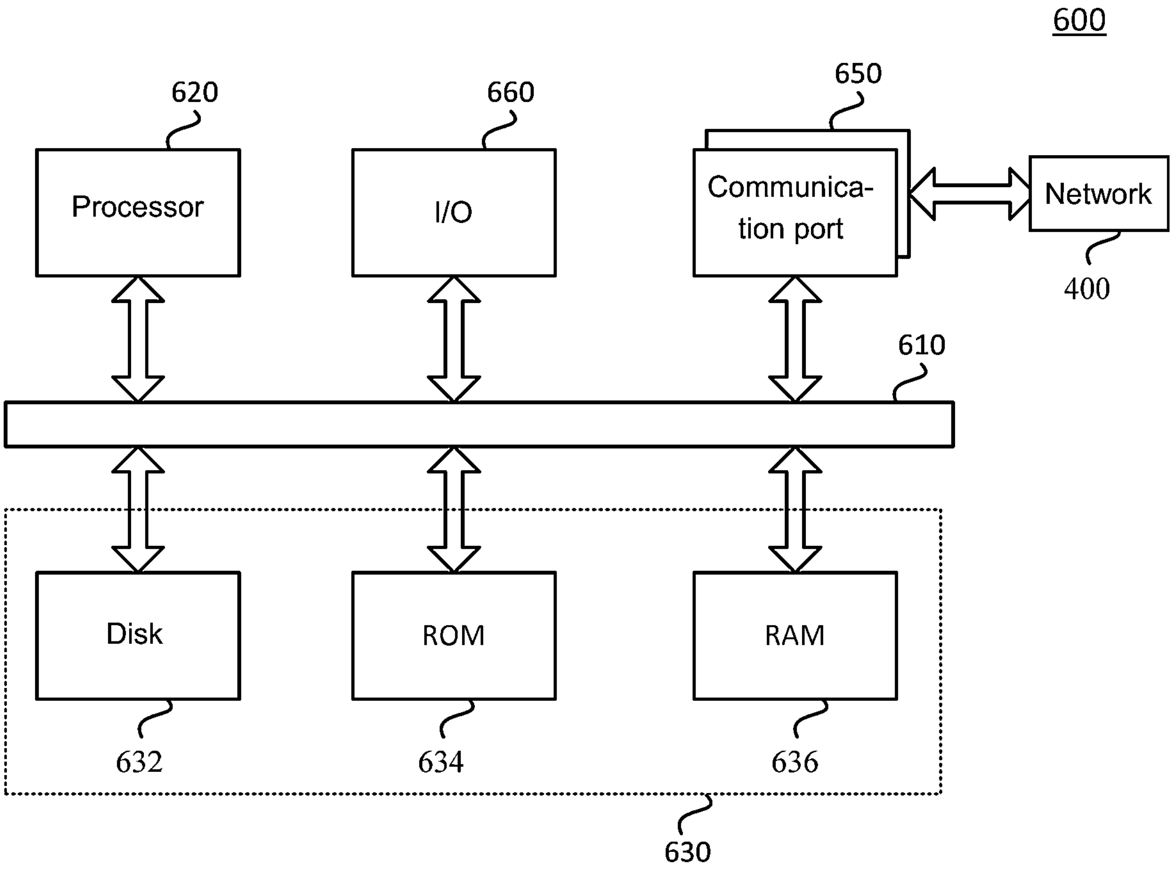
FIG. 3 is a hardware architecture diagram of a computing device according to some exemplary embodiments of the present disclosure.

FIG. 3 illustrates the hardware architecture diagram of a computing device 600 provided according to some exemplary embodiments of the present disclosure. The computing device 600 can execute the method for processing gait data described in the present disclosure. For example, in some exemplary embodiments, at least some steps of the method for processing gait data can be executed on the wearable device 100. In this case, the computing device 600 can be the wearable device 100. In some exemplary embodiments, at least some steps of the method for processing gait data can be executed on the control device 200. In this case, the computing device 600 can be the control device 200. In some exemplary embodiments, at least some steps of the method for processing gait data can be executed on the server 300. In this case, the computing device 600 can be the server 300.

As shown in FIG. 3, the computing device 600 may include at least one storage medium 630 and at least one processor 620. In some exemplary embodiments, the computing device 600 may also include a communication port(s) 650 and an internal communication bus 610. Additionally, the computing device 600 may include I/O components 660. In some exemplary embodiments, when the computing device 600 is a wearable device 100, it may also include a sensor(s) (not shown in FIG. 3).

The internal communication bus 610 can connect different system components. For example, the processor 620, storage medium 630, and communication ports 650 can be connected via the internal communication bus 610.

The I/O components 660 facilitate input and output between the computing device 600 and other components.

The communication ports 650 are used for data communication between the computing device 600 and the external world. For example, the communication ports 650 can be used for data communication between the computing device 600 and the network 400. The communication ports 650 can be either wired or wireless communication ports.

The storage medium 630 can include data storage devices. These data storage devices can be either non-transitory or transitory storage media. For instance, the data storage devices can include one or more of the following: a disk 632, a read-only memory (ROM) 634, or a random access memory (RAM) 636. The storage medium 630 may also include at least one set of instructions stored in the data storage device. This set of instructions includes computer program code that can include programs, routines, objects, components, data structures, processes, modules, etc., for executing the method for processing gait data provided by the present disclosure.

At least one processor 620 may be utilized to execute the aforementioned at least one set of instructions. When the computing device 600 is operational, at least one processor 620 reads the at least one set of instructions and, based on the instructions provided by the at least one set of instructions to execute the method for processing gait data provided by the present disclosure. The processor 620 can execute all or part of the steps contained in the method for processing gait data. The processor 620 can take the form of one or more processors. In some exemplary embodiments, the processor 620 can include one or more hardware processors, such as microcontrollers, microprocessors, reduced instruction set computers (RISC), application-specific integrated circuits (ASICs), application-specific instruction set processors (ASIPs), central processing units (CPUs), graphics processing units (GPUs), physics processing units (PPUs), microcontroller units, digital signal processors (DSPs), field-programmable gate arrays (FPGAs), advanced RISC machines (ARMs), programmable logic devices (PLDs), any circuit or processor capable of performing one or more functions, or any combination thereof. For illustrative purposes only, a single processor 620 is described in the computing device 600 in the present disclosure. However, it should be noted that the computing device 600 in the present disclosure can also include multiple processors. Thus, the operations and/or method steps disclosed in the present disclosure can be executed by a single processor, as described in the present disclosure, or by multiple processors acting together. For example, if the processor 620 of the computing device 600 in the present disclosure executes steps A and B, it should be understood that steps A and B can also be executed jointly or separately by two different processors 620 (for example, the first processor executes step A, and the second processor executes step B, or the first and second processors jointly execute steps A and B).

Figure 4:
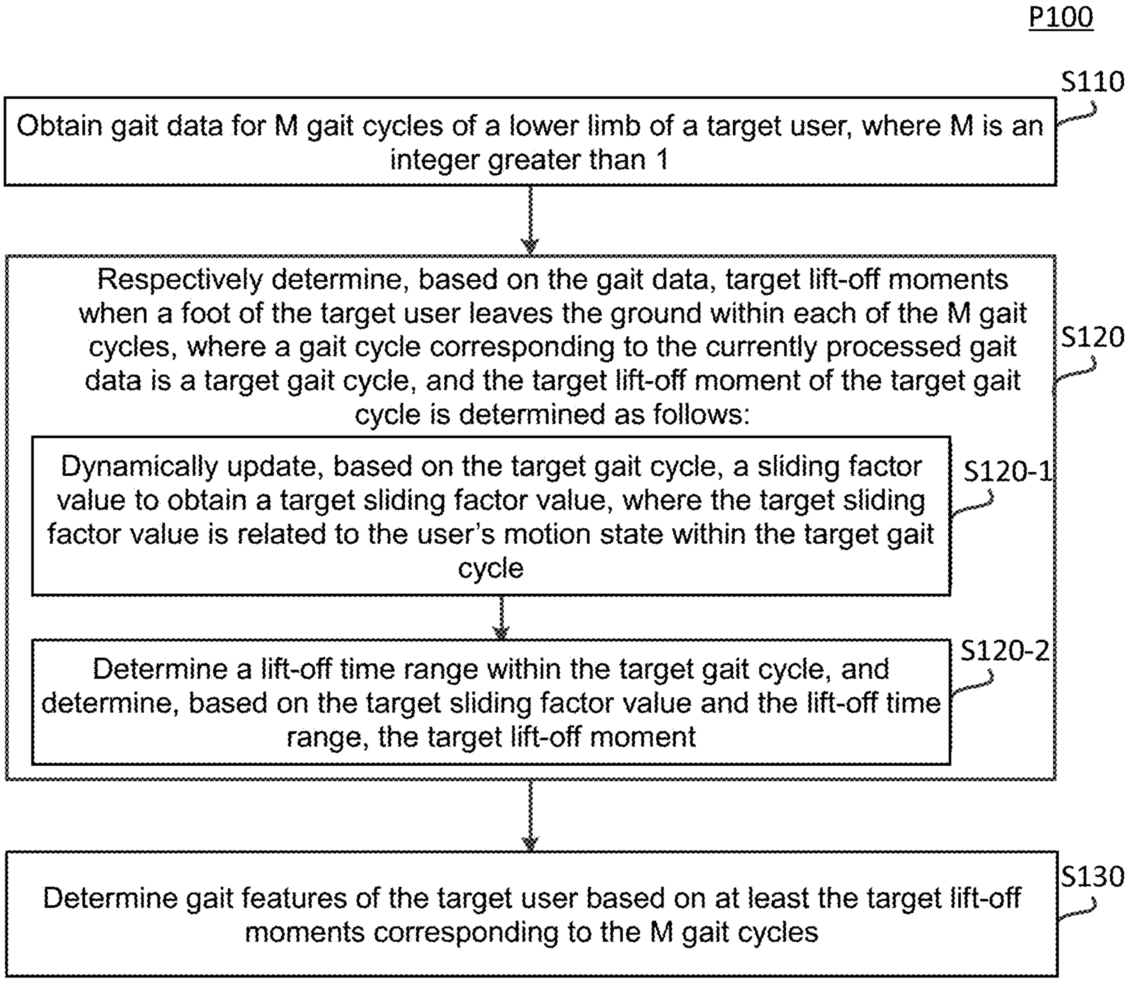
FIG. 4 is a flowchart of a method for processing gait data according to some exemplary embodiments of the present disclosure.

FIG. 4 depicts a flowchart of a gait data processing method P100 provided according to some exemplary embodiments of the present disclosure. As previously mentioned, the computing device 600 can execute the gait data processing method P100 described in the present disclosure. Specifically, the storage medium 630 can store at least one set of instructions for gait data processing; the processor 620 can read and execute the at least one set of instructions, thereby executing the gait data processing method P100 according to the at least one set of instructions. As shown in FIG. 4, the method P100 may include:

S110: Obtain gait data for M gait cycles of a lower limb of a target user, where M is an integer greater than 1.

In some exemplary embodiments, when the computing device 600 is a wearable device 100 (i.e., the wearable device 100 has the structure of the computing device 600), sensors in the computing device 600 can collect gait data of the target user and store the gait data (either persistently or temporarily) in the storage medium 630. Subsequently, the processor 620 can read the gait data from the storage medium 630. In some exemplary embodiments, when the computing device 600 is a control device 200 (i.e., the control device 200 has the structure of the computing device 600), the wearable device 100 collects gait data of the target user via sensors and sends the gait data to the computing device 600. Upon receiving the gait data, the computing device 600 can store the gait data (either persistently or temporarily) in the storage medium 630. Subsequently, the processor 620 can read the gait data from the storage medium 630.

Figure 5:
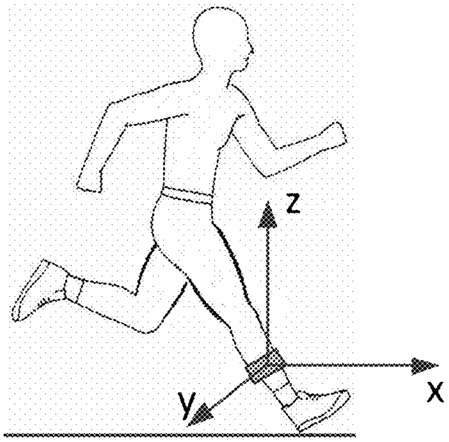
FIG. 5 is a schematic diagram of a spatial coordinate system according to some exemplary embodiments of the present disclosure.

The gait data herein refers to data used to describe the motion and posture of the target user's lower limbs. In some exemplary embodiments, the gait data may include at least one of the following: first acceleration data along the x-axis, second acceleration data along the z-axis, and angular velocity data around the y-axis. Herein, the x-axis, y-axis and z-axis refer to the coordinate axes of a spatial coordinate system. FIG. 5 illustrates a schematic diagram of a spatial coordinate system provided according to some exemplary embodiments of the present disclosure. As shown in FIG. 5, the x-axis points towards the direction the target user is facing, the z-axis points vertically upwards, and the y-axis is perpendicular to both the x-axis and the z-axis, meaning it points to the left or right side of the target user.

It should be understood that during a running process of the target user, the lower leg swings forward rapidly after the foot leaves the ground, causing more obvious changes in the acceleration in the x-axis and the angular velocity around the y-axis. For example, the acceleration in the x-axis can rapidly increase, and the angular velocity around the y-axis can also increase rapidly. Therefore, the first acceleration data in the x-axis and the angular velocity data around the y-axis can be used to determine the moment when the foot of the target user leaves the ground (i.e., the occurrence time of the lift-off event). In addition, during the running process of the target user, before the foot contacts the ground, the acceleration in the z-axis is equal to the gravitational acceleration. After the foot begins to contact the ground, the acceleration in the z-axis undergoes a more obvious change. For example, the acceleration in the z-axis can be affected by the ground reaction force and undergo a reverse change. Therefore, the second acceleration data in the z-axis can be used to determine the moment when the foot of the target user begins to contact the ground (i.e., the occurrence time of the ground contact event).

It should be noted that the gait data can be raw data collected by sensors or data processed in some way from the raw data. For example, the form of gait data can be data pairs in the format of (sampling point identifier, gait sample value), where there is a corresponding relationship between the sampling point identifier and the sampling time since the sampling frequency of the sensor is known. Another example is that the form of gait data can also be data pairs in the format of (sampling time, gait sample value). It should be understood that the form of gait data can also be other data formats, and the present disclosure does not limit this.

The gait of the target user during walking or running exhibits periodicity. The processor 620 can obtain gait data for M gait cycles, where M is an integer greater than 1. It should be noted that the aforementioned M gait cycles can be either contiguous or non-contiguous. For example, in some exemplary embodiments, assuming that the sensors collect gait data for N gait cycles, the processor 620 can resample the gait data of the aforementioned N gait cycles (for example, extracting the 1st, 3rd, 5th, . . . , 2k+1th gait cycles) to obtain gait data for M gait cycles.

S120: Respectively determine, based on the gait data, target lift-off moments when a foot of the target user leaves the ground in each of the M gait cycles.

The processor 620 can process the gait data in each gait cycle separately to determine the target lift-off time/moment when the foot of the target user leaves the ground in that gait cycle. In some exemplary embodiments, the processing method P100 provided by the present disclosure may also include segmenting the gait data into gait cycles to determine the starting and ending positions of each gait cycle. In other words, the processor 620 can separately identify the gait data in each gait cycle. It is understood that the processor 620 segments the gait data to identify the start and end positions of each gait cycle, facilitating subsequent processing of the gait data according to gait cycles. It should be understood that when the processor 620 processes the gait data according to gait cycles, the processing between different gait cycles can be sequential or parallel, and the present disclosure does not limit this issue.

For ease of description, the gait cycle currently being processed corresponding to the gait data is referred to as the target gait cycle. It should be understood that the target gait cycle can be any one of the M gait cycles. The process of determining the target lift-off time/moment corresponding to the target gait cycle includes:

S120-1: Dynamically update, based on the target gait cycle, a sliding factor value to obtain a target sliding factor value, where the target sliding factor value is related to the user's motion state in the target gait cycle; and

S120-2: Determine a lift-off time range in the target gait cycle, and determine, based on the target sliding factor value and the lift-off time range, the target lift-off moment.

In the solution provided by the present disclosure, the processor 620 can preliminarily determine the lift-off time range in the target gait cycle. This lift-off time range refers to the approximate time range during which the foot of the target user leaves the ground in the target gait cycle (i.e., the occurrence time of the lift-off event, which can be abbreviated as the lift-off moment). For example, assuming the starting time of the lift-off time range is T1 and the ending time is T2, it indicates that the foot of the target user leaves the ground in the time range [T1, T2].

The present disclosure introduces the concept of a sliding factor. The sliding factor is used to determine the lift-off moment in the lift-off time range, i.e., to determine the lift-off moment T3 between the starting time T1 and the ending time T2. The value of the sliding factor is a proportional coefficient used to characterize the relationship between the gait sampling values corresponding to the starting time T1, ending time T2, and lift-off moment T3, respectively. In some exemplary embodiments, the sliding factor can have a range of [0, 1]. Assuming the value of the sliding factor is denoted as A, the value of the sliding factor A can be represented by the following formula (1):

$$A = \frac{f(T3) - f(T1)}{f(T2) - f(T1)} \tag{1}$$

Where f(T1) represents the gait sampling value corresponding to the starting time T1, f(T2) represents the gait sampling value corresponding to the ending time T2, and f(T3) represents the gait sampling value corresponding to the lift-off moment T3.

The sliding factor can correspond to different values in different gait cycles. The value corresponding to the sliding factor in each gait cycle is related to the user's motion state in that gait cycle. The user's motion state referred to can be either the motion state of the user recorded in the gait data in that gait cycle or the user's motion state obtained by other means. In some exemplary embodiments, when the processor 620 processes the gait data for each gait cycle, it can dynamically update the value of the sliding factor based on the user's motion state in that gait cycle to obtain the target sliding factor value thereof, and then, based on the target sliding factor value, determine the lift-off moment in the lift-off time range. It can be understood that since the value of the sliding factor is dynamically updated to a value related to the current user's motion state in each gait cycle, the lift-off moment determined in the lift-off time range based on the updated value of the sliding factor (i.e., the target sliding factor value) can be more accurate.

In some exemplary embodiments, the value of the sliding factor may be related to the motion speed of the target user. In this case, the processor 620 can dynamically update the value of the sliding factor based on the motion speed of the target user in the target gait cycle to obtain the target sliding factor value, where the target sliding factor value is inversely proportional (negatively correlated) to the motion speed. In other words, the larger the motion speed of the target user in the target gait cycle, the smaller the target sliding factor value, and the smaller the motion speed of the target user in the target gait cycle, the larger the target sliding factor value. In some exemplary embodiments, the relationship between the target sliding factor value and the motion speed can be represented by a function A=fun1(V), where function fun1 can be a linear function or a non-linear function. In some exemplary embodiments, the relationship between the target sliding factor value A and the motion speed V of the target user can be as shown in Table 1 below. It should be understood that Table 1 only illustrates some target sliding factor values corresponding to certain motion speeds.

TABLE 1

| Motion speed (V) | Target sliding factor value (A) |
|---|---|
| 6 km/h | 0.9 |
| 8 km/h | 0.8 |
| 10 km/h | 0.25 |
| 12 km/h | 0.2 |

In some exemplary embodiments, the processor 620 can determine the motion speed of the target user in the target gait cycle based on the gait data of the target gait cycle or, alternatively, based on the gait data of a predefined number of historical gait cycles before the target gait cycle. Subsequently, the processor 620 can update the value of the sliding factor based on the motion speed of the target user in the target gait cycle, thereby obtaining the target sliding factor value.

In some exemplary embodiments, the processor 620 can also update the value of the sliding factor in the following manner: dynamically updating the value of the sliding factor based on the time difference (i.e., time gap, also referred to as time interval) between a first candidate lift-off moment and a second candidate lift-off moment in the target gait cycle to obtain the target sliding factor value, where the target sliding factor value is inversely proportional to the time difference. In other words, the smaller the time difference between the first candidate lift-off moment and the second candidate lift-off moment, the larger the target sliding factor value; conversely, the larger the time difference between the first candidate lift-off moment and the second candidate lift-off moment, the smaller the target sliding factor value. For example, in some exemplary embodiments, the relationship between the target sliding factor value A and the time difference X can be represented by a function A=fun2(X), where fun2 can be a linear function or a non-linear function.

The aforementioned first candidate lift-off moment and second candidate lift-off moment can be obtained using a predefined search method, which preliminarily searches for candidate lift-off moments in the gait data of the target gait cycle. The predefined search method refers to a method of searching for lift-off events that is not based on the sliding factor. In some exemplary embodiments, the first candidate lift-off moment can be obtained using a predefined search method based on the angular velocity data around the y-axis. For example, the first candidate lift-off moment can be obtained as follows: determining a first search interval in the angular velocity data around the y-axis corresponding to the target gait cycle, and identifying a peak moment of the angular velocity data in the first search interval as the first candidate lift-off moment, where the first search interval is located after the ground contact moment in the target gait cycle.

Figure 6:
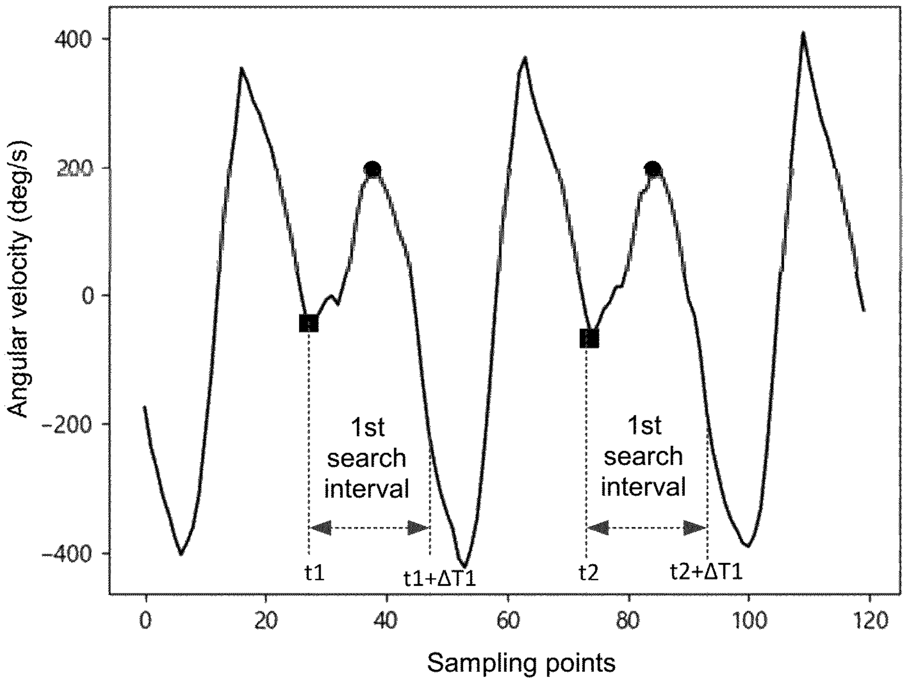
FIG. 6 is a schematic diagram illustrating a first candidate lift-off time determined from angular velocity data around the y-axis according to some exemplary embodiments of the present disclosure.

For easy understanding, further description is made with reference to FIG. 6. FIG. 6 depicts a schematic diagram of the first candidate lift-off moment determined based on the angular velocity data around the y-axis, as provided in some embodiments of the present disclosure. As shown in FIG. 6, since the lift-off event of the target user's foot occurs after the foot contacts the ground (i.e., the ground contact event), a predetermined duration after the ground contact moment of the target user's foot (i.e., the moment of the ground contact event) can be used as the first search interval. In the example illustrated in FIG. 6, two gait cycles are shown. Taking the first gait cycle as an example, it is assumed that t1 represents the ground contact moment of the target user's foot (marked with a black rectangular block in FIG. 6), and ΔT1 is the predetermined duration; in this case, [t1, t1+ΔT1] can be considered as the first search interval. Since the lower leg of the target user swings forward rapidly after the foot leaves the ground, causing the angular velocity to reach its maximum value in a very short period, the maximum value of the angular velocity (i.e., the peak, marked with a black dot in FIG. 6) can be searched in the first search interval [t1, t1+ΔT1]. The moment of the maximum value is then determined as the first candidate lift-off moment. It should be understood that a similar approach can be employed to determine the first candidate lift-off moment for the second gait cycle depicted in FIG. 6, and this disclosure does not elaborate on this further.

In some exemplary embodiments, the second candidate lift-off moment can be obtained using a predefined search method based on the first acceleration data along the x-axis. For example, the second candidate lift-off moment can be obtained as follows: determining the second search interval in the first acceleration data along the x-axis corresponding to the target gait cycle, and identifying the moment of a trough before the peak moment in the first acceleration data in the second search interval as the second candidate lift-off moment, where the second search interval is located after the ground contact moment in the target gait cycle.

Figure 7:
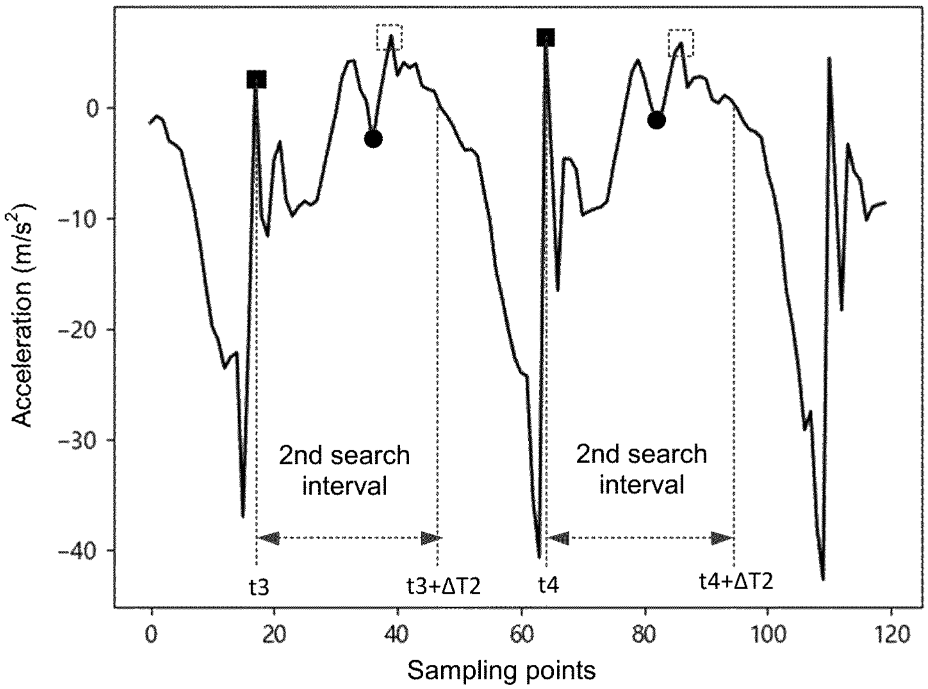
FIG. 7 is a schematic diagram illustrating a second candidate lift-off time determined from first acceleration data along the x-axis according to some exemplary embodiments of the present disclosure.

For easy understanding, further description is made with reference to FIG. 7. FIG. 7 illustrates a schematic diagram of the second candidate lift-off moment determined based on the first acceleration data along the x-axis, as provided in some embodiments of the present disclosure. As shown in FIG. 7, since the lift-off event of the target user's foot occurs after the foot contacts the ground (i.e., the ground contact event), a predetermined duration after the ground contact moment of the target user's foot (i.e., the moment of the ground contact event) can be used as the second search interval. In the example illustrated in FIG. 7, two gait cycles are shown. Taking the first gait cycle as an example, it is assumed that t3 represents the ground contact moment of the target user's foot (marked with a black rectangular block in FIG. 7), and ΔT2 is the predetermined duration. In this case, [t3, t3+ΔT2] can be considered as the second search interval. Since the target user's foot rapidly moves forward after leaving the ground, causing the acceleration along the x-axis to rapidly increase to its maximum value, the maximum value of the acceleration (i.e., the highest peak, marked with a dashed box in FIG. 7) can be searched in the second search interval [t3, t3+ΔT2]. The moment of the first minimum value (i.e., the trough, marked with a black dot in FIG. 7) before the maximum value is then determined as the second candidate lift-off moment. It should be understood that a similar approach can be employed to determine the second candidate lift-off moment for the second gait cycle depicted in FIG. 7, and this disclosure does not elaborate on this further.

With studying the actual running processes of a large number of users, it has been found that the gait sampling values corresponding to the moment when the user's foot leaves the ground (i.e., the lift-off moment) do not exhibit distinct features. That is, they neither manifest as troughs nor as peaks but rather lie between them. Thus, it can be observed that the first and second candidate lift-off moments determined by the predefined search method mentioned earlier both entail certain errors. Furthermore, it has been found through further research that despite the presence of errors in both the first and second candidate lift-off moments, the time difference (or time gap, also referred to as time interval) between them correlates with the motion speed. Consequently, this time difference can be utilized to approximate the motion speed. Therefore, in scenarios where there is considerable variation in a user's running speed or where obtaining the motion speed is challenging, the processor 620 may dynamically update the sliding factor based on this time difference.

In some exemplary embodiments, the lift-off time range can be determined based on pre-established statistical results. For instance, extensive analysis can be conducted on the gait data of a large number of sample users to statistically determine the position of the lift-off moments of their feet in the gait cycle. Subsequently, based on these statistical results, a general time range in the gait cycle can be identified, which encompasses the lift-off moments of all sample users' feet. In this manner, the processor 620 can determine the lift-off time range in the target gait cycle based on this general time range.

In some exemplary embodiments, the lift-off time range can also be determined based on the gait data in the target gait cycle. For example, if the gait sampling values in a predefined duration before and after the foot of the target user leaves the ground gradually increase, the processor 620 can identify the trough (minimum value) and peak (maximum value) of the gait sampling values in this predefined duration. The moment corresponding to the trough is then determined as the starting moment of the lift-off time range, while the moment corresponding to the peak is determined as the ending moment of the lift-off time range. In another example, if the gait sampling values in the predefined duration before and after the foot of the target user leaves the ground gradually decrease, the processor 620 can identify the peak (maximum value) and trough (minimum value) of the gait sampling values in this predefined duration. The moment corresponding to the peak is then determined as the starting moment of the lift-off time range, while the moment corresponding to the trough is determined as the ending moment of the lift-off time range.

Figure 8:
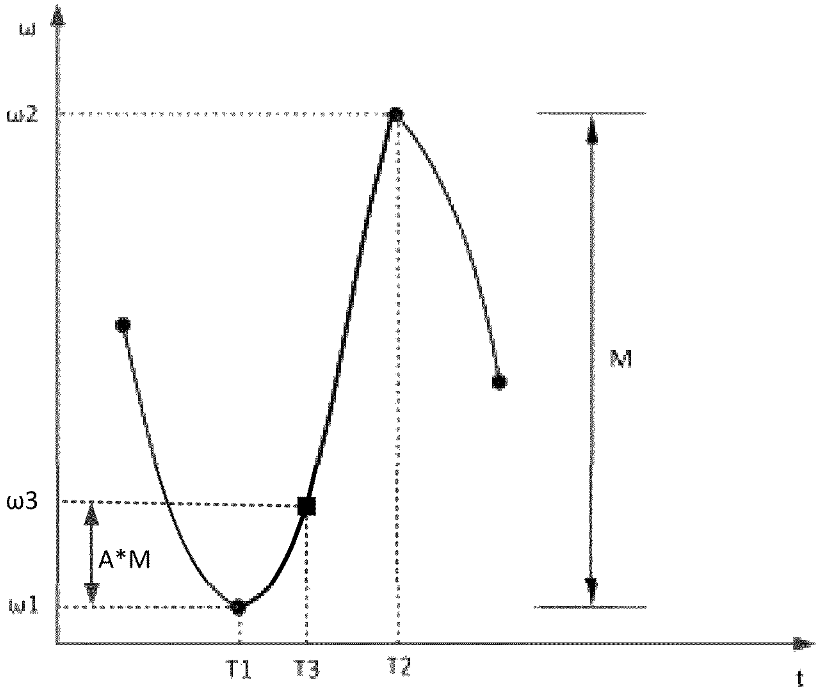
FIG. 8 is a schematic diagram illustrating angular velocity data and a lift-off time range according to some exemplary embodiments of the present disclosure.

In some exemplary embodiments, when the gait data includes angular velocity data around the y-axis, the lift-off time range can be derived from the angular velocity data in the target gait cycle. Considering that during a running process, the swing of the lower leg is minimal when the foot is fully in contact with the ground, resulting in the angular velocity reaching a minimum value at this point. Conversely, after the foot completely leaves the ground, the lower leg swings rapidly forward, causing the angular velocity to reach a maximum value. Therefore, the processor 620 can identify the moment corresponding to the target trough (minimum value) of the angular velocity data in the target gait cycle as the starting moment of the lift-off time range. Similarly, the moment corresponding to the target peak (maximum value) of the angular velocity data in the target gait cycle can be identified as the ending moment of the lift-off time range. It's worth noting that both the target trough and target peak are located after the ground contact moment of the target user's foot in the target gait cycle. For instance, FIG. 8 illustrates a schematic diagram of angular velocity data and the lift-off time range provided in some embodiments of the present disclosure. As depicted in FIG. 8, moment T1 corresponds to the trough of the angular velocity data, while moment T2 corresponds to the peak. The time range between T1 and T2 is considered the lift-off time range.

Based on the angular velocity data and the lift-off time range [T1, T2] mentioned above, the processor 620 can use either of the following methods, Solution 1 and Solution 2, to determine the target lift-off moment.

Solution 1 includes:

(1) Determine a difference between an angular velocity corresponding to an ending moment and an angular velocity corresponding to a starting moment.

Using FIG. 8 as an example, it is assumed that the angular velocity corresponding to the ending moment T2 is ω2, and the angular velocity corresponding to the starting moment T1 is ω1. The difference, denoted as M, is calculated as follows: $M=\omega2-\omega1$.

(2) Determine a target angular velocity based on the target sliding factor value and the difference. The target sliding factor value is denoted as A. The target angular velocity, denoted as ω3, can be calculated using the following formula: $\omega3=A*M+\omega1=A*(\omega2-\omega1)+\omega1$.

(3) Search for the target angular velocity in the lift-off time range, and consider the moment when the target angular velocity occurs as the target lift-off moment.

Continuing with the example in FIG. 8, search for the target angular velocity ω3 between the starting moment T1 and the ending moment T2; then, consider the moment corresponding to the target angular velocity ω3, denoted as T3, as the target lift-off moment.

In the aforementioned scheme 1, the processor 620 can determine the target lift-off moment T3 in the lift-off time range [T1, T2] based on the target sliding factor value A. It's understandable that the specific position of the target lift-off moment T3 in the lift-off time range [T1, T2] can be determined by the target sliding factor value A. For example, the smaller the target sliding factor value A, the closer the target lift-off moment T3 will be to T1 in the lift-off time range [T1, T2]. Conversely, the larger the target sliding factor value A, the closer the target lift-off moment T3 will be to T2 in the lift-off time range [T1, T2]. Since the target sliding factor value A is related to the user's motion state in the current gait cycle, the target lift-off moment determined based on the target sliding factor value A can be more accurate.

Figure 9:
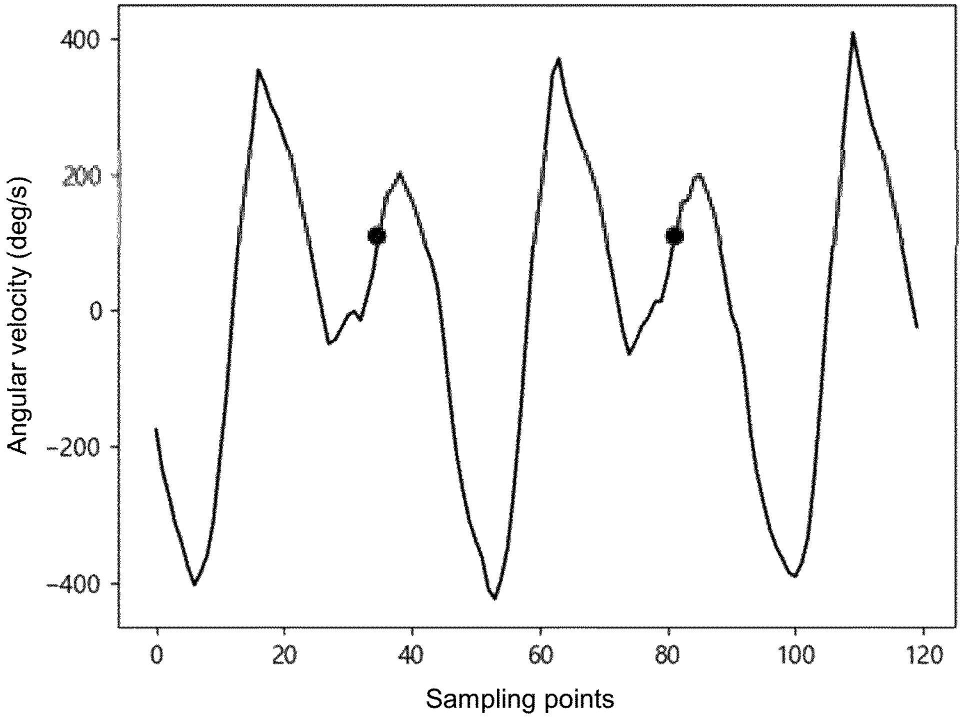
FIG. 9 is a schematic diagram illustrating a target lift-off time determined from angular velocity data based on a target sliding factor according to some exemplary embodiments of the present disclosure.

FIG. 9 illustrates a schematic diagram of the target lift-off moment determined based on the target sliding factor in the angular velocity data, as provided in some exemplary embodiments of the present disclosure. As shown in FIG. 9, the target lift-off moment determined using solution 1 corresponds to the positions marked with black dots. It can be observed that the target lift-off moment determined by solution 1 is located between the trough and the peak. Compared to directly using the trough or the peak as the target lift-off moment, the target lift-off moment determined by solution 1 is more consistent with the actual situation, thereby improving the accuracy of the target lift-off moment.

Solution 2 includes:

(1) Determine a difference between an angular velocity corresponding to an ending moment and an angular velocity corresponding to a starting moment.

(2) Determine, based on the target sliding factor value and the difference the target angular velocity.

(3) Search for the target angular velocity in the lift-off time range, and determine the moment when the target angular velocity occurs as a third candidate lift-off moment.

It should be understood that the implementation of steps (1) to (3) in solution 2 is similar to solution 1, and thus not elaborated herein. The difference between solution 2 and solution 1 lies in the fact that, in solution 2, the processor 620 considers the lift-off moment T3 determined based on the target sliding factor value A in the lift-off time range [T1, T2] as the third candidate lift-off moment, rather than the target lift-off moment.

(4) Determine the target lift-off moment based on the first candidate lift-off moment, the second candidate lift-off moment, and the third candidate lift-off moment in the target gait cycle.

It should be noted that the determination method of the first candidate lift-off moment and the second candidate lift-off moment has been explained in the previous relevant section, and hence will not be reiterated herein.

In some exemplary embodiments, the processor 620 can determine the target lift-off moment by averaging or weighted averaging the first candidate lift-off moment, the second candidate lift-off moment, and the third candidate lift-off moment. It's understandable that these exemplary embodiments improve the accuracy of the target lift-off moment by considering the results of multiple lift-off event search methods.

In some exemplary embodiments, the processor 620 may execute a first processing mode or a second processing mode based on the timing relationship between the first candidate lift-off moment and the second candidate lift-off moment. The first processing mode includes: setting the average of the second candidate lift-off moment and the third candidate lift-off moment as the target lift-off moment, or setting the average of the first candidate lift-off moment, the second candidate lift-off moment, and the third candidate lift-off moment as the target lift-off moment. The second processing mode includes: setting the average of the third candidate lift-off moment as the target lift-off moment.

In some exemplary embodiments, if the first candidate lift-off moment is earlier than or equal to the second candidate lift-off moment, then the processor 620 executes the first processing mode as described above. In some exemplary embodiments, if the first candidate lift-off moment is later than the second candidate lift-off moment, then processor 620 executes the second processing mode as described above.

As mentioned earlier, the time difference between the first candidate lift-off moment and the second candidate lift-off moment is related to the user's motion speed. According to actual test results, it can be observed that "the first candidate lift-off moment is earlier than or equal to the second candidate lift-off moment" corresponds to situations where the user's motion speed is relatively low, such as when the user's running speed is less than or equal to 6 km/h. In this case, the first candidate lift-off moment and/or the second candidate lift-off moment can achieve a certain level of accuracy. Therefore, the average of the first candidate lift-off moment and the third candidate lift-off moment, or the average of the first candidate lift-off moment, the second candidate lift-off moment, and the third candidate lift-off moment, can be set as the target lift-off moment. This approach integrates the results of multiple lift-off event search methods, thereby improving the measurement accuracy of the target lift-off moment. On the other hand, "the first candidate lift-off moment is later than the second candidate lift-off moment" corresponds to situations where the user's motion speed is relatively high, such as when the user's running speed is greater than 6 km/h. In this case, the accuracy of the first candidate lift-off moment and the second candidate lift-off moment is not high. Therefore, the third candidate lift-off moment can be set as the target lift-off moment to improve the measurement accuracy of the target lift-off moment.

S130: Determine gait features of the target user based on at least the target lift-off moments corresponding to the M gait cycles.

It can be understood that the processor 620 is capable of analyzing M target lift-off moments corresponding to M gait cycles, and through this analysis, it can determine the gait features of the target user. In some exemplary embodiments, these gait features of the target user may include: gait balance, running efficiency, and features of at least one dimension of vertical amplitude. Gait balance is an important indicator used to measure the balance of muscle strength on the left and right sides and overall body coordination. Running efficiency is an indicator used to measure running economy, referring to the ability to maximize energy utilization. For example, with the same energy consumption, higher running efficiency results in faster and farther running. Or, with the same speed and distance, higher running efficiency leads to less energy consumption. Vertical amplitude refers to the height of the body's center of gravity vertical movement during running. To some extent, it also reflects running efficiency. For instance, larger vertical amplitudes indicate lower running efficiency, while smaller vertical amplitudes indicate higher running efficiency.

In some exemplary embodiments, the method P100 for processing gait data provided by the present disclosure may further include: S125: based on the gait data, respectively determining the ground contact moment of the target user's feet in the M gait cycles. In this way, the processor 620 can determine the gait features of the target user based on the target lift-off moment and ground contact moment corresponding to the M gait cycles. It should be noted that S125 is not illustrated in FIG. 4, and S125 can be executed before S120, after S120, or concurrently with S120.

In some exemplary embodiments, the gait data may include second acceleration data along the z-axis. In this case, the processor 620 may process the gait data for each gait cycle separately to determine the ground contact moment of the target user's foot in each gait cycle. The gait cycle currently being processed corresponding to the gait data is referred to as the target gait cycle. The process of determining the ground contact moment corresponding to the target gait cycle includes: identifying a first trough moment before a peak moment of the second acceleration data corresponding to the target gait cycle as the ground contact moment.

Figure 10:
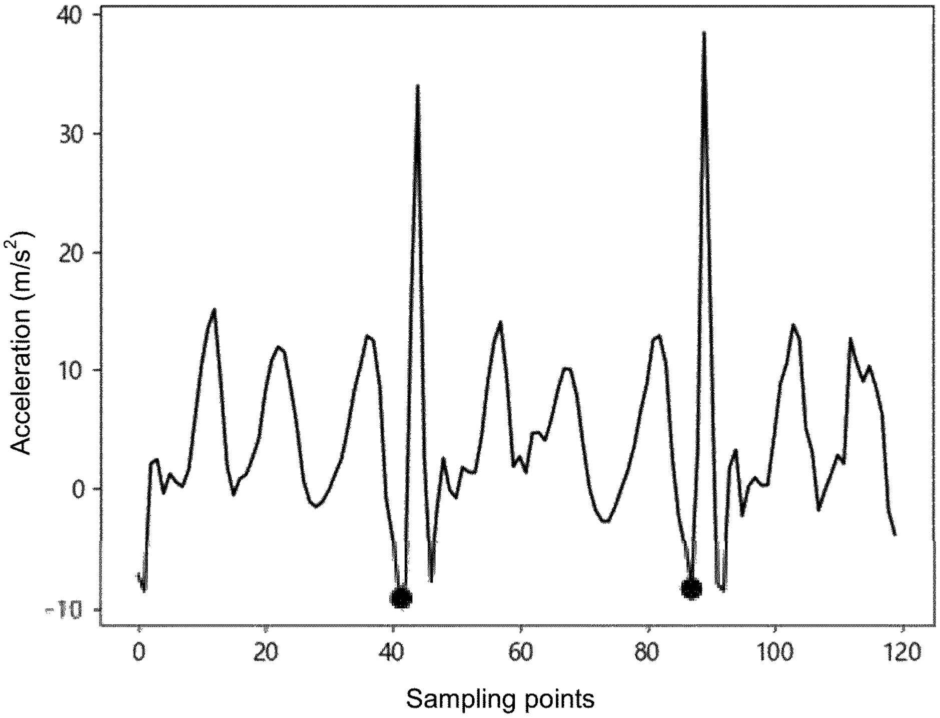
FIG. 10 is a schematic diagram illustrating a ground contact time determined from second acceleration data along the z-axis according to some exemplary embodiments of the present disclosure.

For better understanding, FIG. 10 will be used as an example for further description. FIG. 10 depicts a schematic diagram illustrating the determination of ground contact moments in the second acceleration data along the z-axis according to some exemplary embodiments of the present disclosure. As shown in FIG. 10, one can first identify the occurrence moment of the peak in the second acceleration data, then search for the occurrence moment of the first trough before the peak occurrence moment, and designate this trough occurrence moment as the ground contact moment. In FIG. 10, the acceleration sample values corresponding to the ground contact moments are marked with black dots. It should be understood that during actual running, the foot makes contact with the ground and then quickly pushes off, causing the acceleration along the z-axis to reverse and rapidly reach its maximum value. Therefore, the ground contact moment exhibits a distinctive feature in the second acceleration data, represented by the first trough before the peak. Consequently, by determining the occurrence moment of the first trough before the peak in the second acceleration data as the ground contact moment, this method ensures a higher accuracy of ground contact moment identification.

In some exemplary embodiments, the processor 620 can determine the ground contact duration for the M gait cycles based on the target lift-off moments and ground contact moments corresponding to each of these cycles. Specifically, for each gait cycle, the processor 620 can subtract the ground contact moment from the target lift-off moment to obtain the ground contact duration corresponding to that gait cycle. Subsequently, based on the ground contact durations corresponding to the M gait cycles, the processor 620 can determine the gait features of the target user. In some exemplary embodiments, the processor 620 can determine the running efficiency of the target user based on the ground contact durations corresponding to the M gait cycles.

In some exemplary embodiments, the processor 620 can also determine the off-ground duration for the M gait cycles based on the target lift-off moments and ground contact moments corresponding to each of these cycles. Subsequently, the processor 620 can use the off-ground durations corresponding to the M gait cycles to determine the gait features of the target user. In some exemplary embodiments, the processor 620 can determine the running efficiency of the target user based on the off-ground durations corresponding to the M gait cycles.

In some exemplary embodiments, the processor 620 can separately obtain the ground contact durations for the left foot across M gait cycles, as well as the ground contact durations for the right foot across M gait cycles. Subsequently, based on the ground contact durations for the left foot across M gait cycles and the ground contact durations for the right foot across M gait cycles, the processor 620 can determine the gait balance.

In some exemplary embodiments, when the computing device 600 includes a display screen, the processor 620 can, after determining the gait features of the target user, display these gait features on the screen. For example, the gait features can be displayed using text, or using visual elements such as graphs, tables, and so on. By displaying these gait features, the system 001 enables the target user to become aware of their own gait features, thereby facilitating timely corrections to their exercise posture.

In some exemplary embodiments, when the computing device 600 includes an audio output device (such as a speaker), the processor 620 can, after determining the gait features of the target user, play these gait features via voice with the audio output device. It's understood that the system 001 enables the target user to become aware of their own gait features through voice playback, thereby facilitating timely corrections to their exercise posture. Additionally, this method is convenient as it doesn't require the user to look at a screen, allowing users to receive real-time updates on their gait features and make adjustments while exercising, thus enhancing running efficiency.

Furthermore, the computing device 600 can also communicate with a target device. For instance, if the computing device 600 is a wearable device 100, the target device mentioned above could be a control device 200. Alternatively, if the computing device 600 is a control device 200, the target device could be another terminal device connected to the control device 200, such as headphones, smart screens, etc. After determining the gait features of the target user, the processor 620 can send these gait features to the target device, which can then either play them back via voice or display them, depending on the circumstances. This way, the appropriate output method for the gait features based on the current scenario can be utilized, enabling users to become aware of their own gait features in different situations and facilitating timely corrections to their exercise posture.

Figure 11:
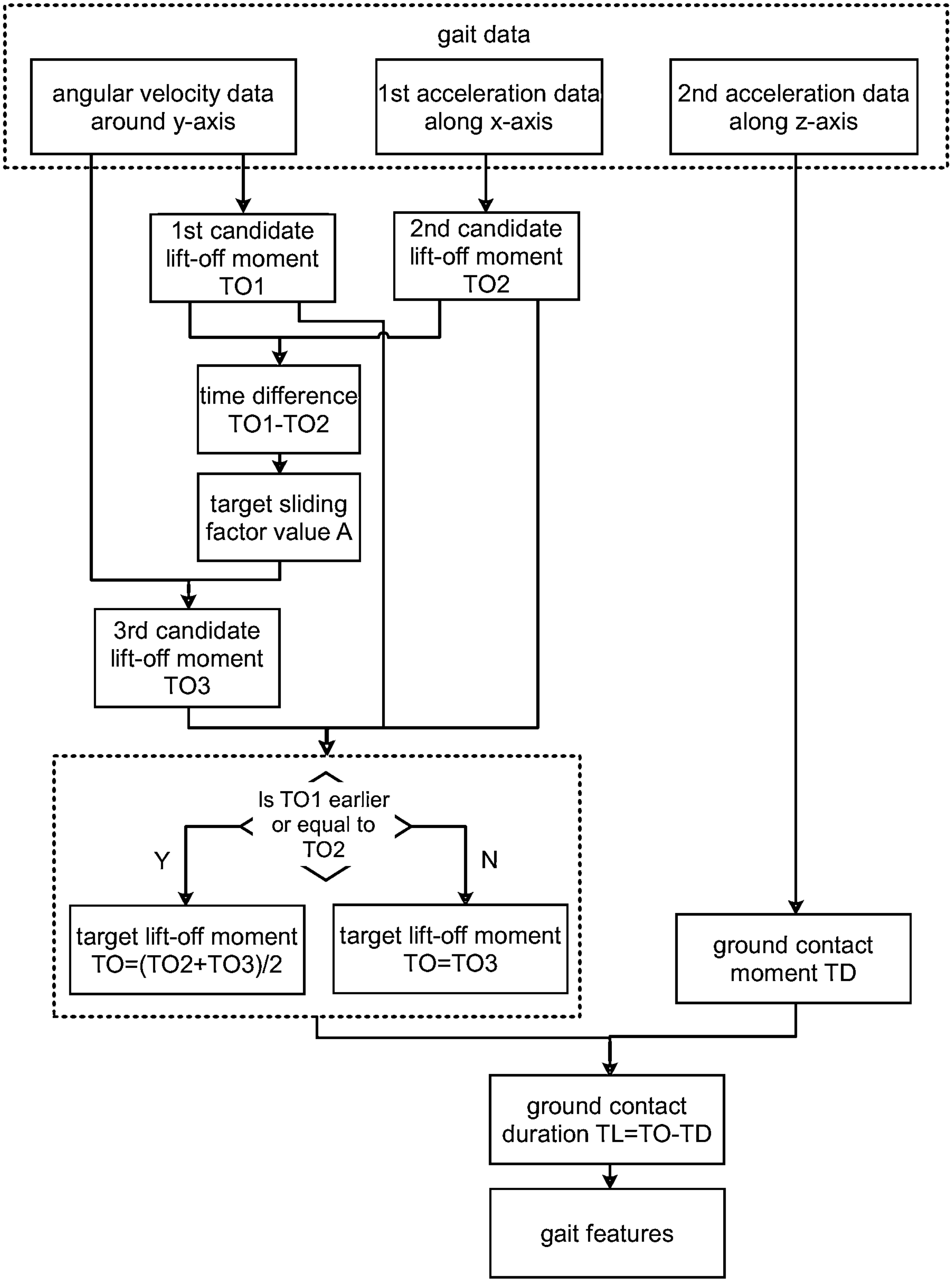
FIG. 11 is a schematic diagram illustrating a processing process of gait data according to some embodiments of the present disclosure.

FIG. 11 illustrates a schematic diagram of a gait data processing procedure provided according to some exemplary embodiments of the present disclosure. As shown in FIG. 11, the gait data processing procedure includes:

(1) The processor 620 obtains gait data for M gait cycles of a target user's lower limbs, the gait data includes: first acceleration data along the x-axis, second acceleration data along the z-axis, and angular velocity data around the y-axis.

(2) The processor 620 processes the gait data in each gait cycle separately to determine a ground contact moment TD and a lift-off moment TO for the target user's foot in each gait cycle.

For the ground contact moment TD, the processor 602 utilizes a search method for ground contact events as shown in FIG. 10 to search for it in the current gait cycle.

For the target lift-off moment TO, the processor 602 obtain it using the following method:

(a) Based on the angular velocity data around the y-axis, the processor utilizes the lift-off event search method shown in FIG. 6 to determine a first candidate lift-off moment TO1 in the current gait cycle.

(b) Based on the first acceleration data along the x-axis, the processor utilizes the lift-off event search method shown in FIG. 7 to determine a second candidate lift-off moment TO2 in the target gait cycle.

(c) Determine a time difference between the first candidate lift-off moment and the second candidate lift-off moment (TO1−TO2).

(d) Dynamically update the value of a sliding factor based on the time difference (TO1−TO2) to obtain the target sliding factor value A.

(e) Based on the angular velocity data around the y-axis, determine the lift-off time range in the current gait cycle, and based on the target sliding factor value A, determine a third candidate lift-off moment TO3 in the lift-off time range.

(f) Based on the first candidate lift-off moment TO1, the second candidate lift-off moment TO2, and the third candidate lift-off moment TO3, determine the target lift-off moment TO in the current gait cycle. If the first candidate lift-off moment TO1 is earlier than or equal to the second candidate lift-off moment TO2, the processor 620 calculates the target lift-off moment TO as the average of the second candidate lift-off moment TO2 and the third candidate lift-off moment TO3, i.e., TO=(TO2+TO3)/2. If the first candidate lift-off moment TO1 is later than the second candidate lift-off moment TO2, then the processor 620 determines the third candidate lift-off moment TO3 as the target lift-off moment, i.e., TO=TO3.

(3) Based on the target lift-off moment TO and ground contact moment TD corresponding to each of the M gait cycles, the processor 620 determines the ground contact duration TL for each gait cycle as TL=TO−TD.

(4) Based on the ground contact duration TL corresponding to each of the M gait cycles, the processor 620 determines the gait features of the target user.

It should be understood that the specific implementation of each step in the gait data processing procedure shown in FIG. 11 has been introduced in the relevant sections of the previous text and will not be reiterated herein.

To assess the effectiveness of the solutions in the present disclosure, gait data of a target user has been collected during running at different speeds (6 km/h, 8 km/h, and 10 km/h) in experiments. The collected gait data is then processed according to the procedure shown in FIG. 11, resulting in ground contact durations corresponding to different running speeds. Subsequently, the ground contact durations obtained based on the present disclosure scheme are compared with those measured by a force sensing treadmill, and the test results are presented in Table 2 below. As shown in Table 2, the average error between the ground contact durations obtained by the solutions of the present disclosure and those measured by the force sensing treadmill is 10 ms, indicating that the ground contact durations obtained by the present disclosure exhibit high accuracy.

TABLE 2

| Running speed | Target sliding factor value | Ground contact duration obtained by the present disclosure | Ground contact duration measured by treadmill | Error |
|---|---|---|---|---|
| 6 km/h | 0.9 | 458 ms | 452 ms | 6 ms |
| 8 km/h | 0.8 | 377 ms | 361 ms | 16 ms |
| 10 km/h | 0.25 | 317 ms | 309 ms | 8 ms |

It should be noted that the gait analysis process described in the present disclosure can be performed in real-time, meaning that after sensors collect gait data for one gait cycle, the processor 620 immediately processes the gait data for that gait cycle. The gait analysis process described in the present disclosure can also be performed non-real-time, meaning that sensors collect gait data for multiple gait cycles in a preset duration, and after the preset duration ends, the processor 620 then processes the gait data for the multiple gait cycles.

In summary, by executing the processing method P100 of gait data provided in the present disclosure, the system 001 can obtain gait data for M gait cycles of a target user's lower limb(s). Based on the gait data, the target lift-off moment when the user's foot leaves the ground is determined for each of the M gait cycles. Gait features of the target user are then determined based on at least the target lift-off moments corresponding to each of the M gait cycles. During the processing of gait data, the system 001 dynamically updates the value of the sliding factor for each gait cycle to obtain the target sliding factor value. This target sliding factor value is associated with the user's motion state in that gait cycle. Consequently, the system 001 determines the lift-off time range in the current gait cycle and identifies the target lift-off moment in that gait cycle based on the target sliding factor value and the lift-off time range. Since the value of the sliding factor is dynamically updated in real-time according to the user's motion state in the current gait cycle, the target lift-off moment determined based on the target sliding factor value is more accurate. Therefore, the gait features determined based on the target lift-off moments are also more accurate. As a result, the gait analysis results have a higher level of accuracy.

In another aspect, the present disclosure further provides a non-transitory storage medium storing at least one set of executable instructions for processing gait data. When the executable instructions are executed by a processor, they guide the processor to implement the steps of the processing method P100 described in the present disclosure. In some exemplary embodiments, various aspects of the present disclosure can also be realized in the form of a program product containing program code. When the program product runs on the computing device 600, the program code is used to cause the computing device 600 to execute the steps of the processing method P100 described in the present disclosure. Program products for implementing the above methods can be in the form of portable compact disc-read only memory (CD-ROM) containing program code, and can run on the computing device 600. However, the program product of the present disclosure is not limited to this. In the present disclosure, the readable storage medium can be any tangible medium containing or storing a program that can be used by an instruction execution system or in conjunction with it. The program product can utilize any combination of one or more readable media. Readable media can be signal media or storage media. Examples of readable storage media include, but are not limited to, systems, devices, or apparatuses of electrical, magnetic, optical, electromagnetic, infrared, or semiconductor nature, or any combination thereof. More specific examples of readable storage media include: electrical connections with one or more wires, portable discs, hard drives, random access memory (RAM), read-only memory (ROM), erasable programmable read-only memory (EPROM or flash memory), optical fibers, portable compact disc-read only memory (CD-ROM), optical storage devices, magnetic storage devices, or any suitable combination thereof. The computer-readable storage medium may include data signals propagated in the baseband or as part of a carrier, carrying readable program code. These propagated data signals can take various forms, including but not limited to electromagnetic signals, optical signals, or any suitable combination thereof. The readable storage medium can also be any readable medium other than a readable storage medium, which can transmit, propagate, or transmit programs for use by an instruction execution system, apparatus, or device, or in conjunction with it. The program code contained on the readable storage medium can be transmitted using any suitable medium, including but not limited to wireless, wired, optical cable, RF, and so forth, or any suitable combination thereof. The program code for performing operations of the present disclosure can be written in any combination of one or more programming languages, including object-oriented programming languages such as Java, C++, as well as conventional procedural programming languages such as "C" or similar programming languages. The program code can be executed entirely on the computing device 600, partially on the computing device 600, as a standalone software package, partially on the computing device 600 and partially on a remote computing device, or entirely on a remote computing device.

The above description pertains to specific embodiments of the present disclosure. Other embodiments are in the scope of the appended claims. In some instances, actions or steps recited in the claims can be performed in a different order than that described in the embodiments and still achieve the desired results. Additionally, processes depicted in the figures do not necessarily require specific or consecutive ordering to achieve the desired results. In certain embodiments, multitasking and parallel processing may also be possible or advantageous.

In summary, after reviewing the contents of this detailed disclosure, a person skilled in the art can understand that the foregoing detailed disclosure is presented by way of example and is not restrictive. Although not explicitly stated, a person skilled in the art can appreciate that the present disclosure encompasses various reasonable changes, improvements, and modifications to the embodiments. These changes, improvements, and modifications are intended to be proposed by the present disclosure and are in the scope of the present disclosure.

Moreover, certain terms in the present disclosure have been used to describe embodiments of the present disclosure. For example, "an embodiment," "embodiments," and/or "some embodiments" mean that the specific features, structures, or characteristics described in conjunction with that embodiment may be included in at least one embodiment of the present disclosure. Thus, it should be emphasized and understood that references to "embodiments" or "an embodiment" or "alternative embodiments" in various parts of the present disclosure may not necessarily refer to the same embodiment. Additionally, specific features, structures, or characteristics may be appropriately combined in one or more embodiments of the present disclosure.

It should be understood that, in the foregoing description of exemplary embodiments of the present disclosure, for the purpose of aiding understanding of a feature, and for simplifying the disclosure, various features are combined in a single embodiment, drawing, or description of the present disclosure. However, this does not imply that the combination of these features is necessary, and a person skilled in the art may understand some of the devices as separate embodiments when reading the present disclosure. In other words, embodiments in the present disclosure can also be understood as integrations of multiple sub-embodiments. In addition, it is also valid for each sub-embodiment to include less than all the features of a single disclosed embodiment.

Every patent, patent application, patent application publication, and other material cited herein, such as articles, books, manuals, publications, documents, items, etc., along with any prosecution histories related thereto, any identical or potentially conflicting materials, or any prosecution histories that may have a limiting impact on the broadest scope of the claims, are incorporated herein by reference in their entirety and for all purposes now or hereafter related to this document. Additionally, in the event of any inconsistency or conflict between the terms, descriptions, definitions, and/or usage of terms associated with any materials referenced herein and those associated with this document, the terms used in this document shall prevail.

Finally, it should be understood that the exemplary embodiments disclosed herein are illustrative of principles of embodiments of the present disclosure. Other modified embodiments are also in the scope of the present disclosure. Therefore, the embodiments disclosed in the present disclosure are provided as examples and not limitations. A person skilled in the art can implement alternative configurations based on the embodiments in the present disclosure. Thus, the embodiments of the present disclosure are not limited to the exemplary embodiments precisely described in the present disclosure.

What is claimed is:

1. A system for gait data processing, comprising:

at least one storage medium storing at least one set of instructions for gait data processing; and at least one processor in communication with the at least one storage medium, wherein during operation, the at least one processor executes the at least one set of instructions to cause the system to at least:

obtain gait data of M gait cycles of a lower limb of a target user, wherein M is an integer greater than 1;

respectively determine, based on the gait data, target lift-off moments when a foot of the target user leaves the ground in the M gait cycles, wherein a gait cycle corresponding to currently processed gait data is a target gait cycle, and a process for determining a target lift-off moment corresponding to the target gait cycle includes:

dynamically updating a sliding factor value according to the target gait cycle to obtain a target sliding factor value, wherein the target sliding factor value is related to a user motion state in the target gait cycle, wherein to dynamically update the sliding factor value according to the target gait cycle to obtain the target sliding factor value, the at least one processor executes the at least one set of instructions to cause the system to at least:

dynamically update, based on a time interval between a first candidate lift-off moment and a second candidate lift-off moment in the target gait cycle, the sliding factor value to obtain the target sliding factor value, wherein the target sliding factor value is negatively correlated to the time interval, and determining a lift-off time range in the target gait cycle and determining the target lift-off moment based on the target sliding factor value and the lift-off time range; and determine a gait feature of the target user based on at least the target lift-off moments corresponding to the M gait cycles.

2. The system according to claim 1, wherein to dynamically update the sliding factor value according to the target gait cycle to obtain the target sliding factor value, the at least one processor executes the at least one set of instructions to cause the system to at least:

dynamically update the sliding factor value based on a motion speed of the target user in the target gait cycle to obtain the target sliding factor value, wherein the target sliding factor value is negatively correlated to the motion speed.

3. The system according to claim 1, wherein the gait data includes angular velocity data around a y-axis perpendicular to a direction the target user is facing; and to determine the lift-off time range in the target gait cycle, the at least one processor executes the at least one set of instructions to cause the system to at least:

determine a moment corresponding to a target trough of the angular velocity data in the target gait cycle as a starting moment of the lift-off time range, and a moment corresponding to a target peak of the angular velocity data in the target gait cycle as an ending moment of the lift-off time range, wherein the target trough and the target peak are both located after a ground contact moment of the foot of the target user in the target gait cycle.

4. The system according to claim 3, wherein to determine the target lift-off moment based on the target sliding factor value and the lift-off time range, the at least one processor executes the at least one set of instructions to cause the system to at least:

determine a difference between an angular velocity corresponding to the ending moment and an angular velocity corresponding to the starting moment;

determine a target angular velocity based on the target sliding factor value and the difference; and search for the target angular velocity in the lift-off time range, and determine a moment corresponding to the target angular velocity as the target lift-off moment.

5. The system according to claim 3, wherein to determine the target lift-off moment based on the target sliding factor value and the lift-off time range, the at least one processor executes the at least one set of instructions to cause the system to at least:

determine a difference between an angular velocity corresponding to the ending moment and an angular velocity corresponding to the starting moment;

determine a target angular velocity based on the target sliding factor value and the difference;

search for the target angular velocity in the lift-off time range, and determine a moment corresponding to the target angular velocity as a third candidate lift-off moment; and determine the target lift-off moment based on the first candidate lift-off moment, the second candidate lift-off moment and the third candidate lift-off moment in the target gait cycle.

6. The system according to claim 5, wherein to determine the target lift-off moment based on the first candidate lift-off moment, the second candidate lift-off moment and the third candidate lift-off moment in the target gait cycle, the at least one processor executes the at least one set of instructions to cause the system to at least:

execute, based on a time relationship between the first candidate lift-off moment and the second candidate lift-off moment, a first processing mode or a second processing mode, wherein the first processing mode includes: determining an average of the second candidate lift-off moment and the third candidate lift-off moment as the target lift-off moment, and the second processing mode includes: determining the third candidate lift-off moment as the target lift-off moment.

7. The system according to claim 6, wherein to execute, based on the time relationship between the first candidate lift-off moment and the second candidate lift-off moment, the first processing mode or the second processing mode, the at least one processor executes the at least one set of instructions to cause the system to at least:

execute the first processing mode upon determining that the first candidate lift-off moment is earlier than or equal to the second candidate lift-off moment; or execute the second processing mode upon determining that the first candidate lift-off moment is later than the second candidate lift-off moment.

8. The system according to claim 1, wherein the gait data includes: first acceleration data along an x-axis and angular velocity data around a y-axis, wherein the x-axis points to a direction the target user is facing, and the y-axis is perpendicular to the x-axis;

the first candidate lift-off moment is determined by: determining a first search interval in the angular velocity data corresponding to the target gait cycle, and determining a peak moment of the angular velocity data in the first search interval as the first candidate lift-off moment, wherein the first search interval is located after a ground contact moment in the target gait cycle; and the second candidate lift-off moment is determined by: determining a second search interval in the first acceleration data corresponding to the target gait cycle, and determining a trough moment before a peak moment of the first acceleration data in the second search interval as the second candidate lift-off moment, wherein the second search interval is located after the ground contact moment in the target gait cycle.

9. The system according to claim 1, wherein the at least one processor executes the at least one set of instructions to further cause the system to at least:

respectively determine, based on the gait data, ground contact moments of the foot of the target user in the M gait cycles; and to determine the gait feature of the target user, the at least one processor executes the at least one set of instructions to cause the system to at least:

determine, based on the target lift-off moments and the ground contact moments corresponding to the M gait cycles, the gait feature of the target user.

10. The system according to claim 9, wherein the gait data includes second acceleration data along a z-axis pointing in a direction perpendicular to the ground; and a ground contact moment corresponding to the target gait cycle is determined by: determining a first trough moment before a peak moment of the second acceleration data corresponding to the target gait cycle as the ground contact moment corresponding to the target gait cycle.

11. The system according to claim 9, wherein to determine, based on the target lift-off moments and the ground contact moments corresponding to the M gait cycles, the gait feature of the target user, the at least one processor executes the at least one set of instructions to cause the system to at least:

determine, based on the target lift-off moments and the ground contact moments corresponding to the M gait cycles, ground contact durations corresponding to the M gait cycles; and determine, based on the ground contact durations corresponding to the M gait cycles, the gait feature of the target user.

12. The system according to claim 1, wherein after determining the gait feature of the target user, the at least one processor further executes the at least one set of instructions to cause the system to perform at least one of:

playing back the gait feature;

displaying the gait feature; or sending the gait feature to a target device to play back or display the gait feature via the target device.

13. The system according to claim 1, wherein the at least one processor further executes the at least one set of instructions to cause the system to at least:

segment the gait data into gait cycles to determine starting and ending positions of each gait cycle.

14. The system according to claim 1, further comprising:

a sensor, wherein the sensor is arranged in a wearable device, the sensor is configured to be worn within a lower limb range of the target user to collect the gait data, and the at least one storage medium and the at least one processor are arranged in the wearable device or in a control device in communication with the wearable device.

15. A method for gait data processing, comprising:

obtaining gait data of M gait cycles of a lower limb of a target user, wherein M is an integer greater than 1;

respectively determining, based on the gait data, target lift-off moments when a foot of the target user leaves the ground in the M gait cycles, wherein a gait cycle corresponding to currently processed gait data is a target gait cycle, and a process for determining a target lift-off moment corresponding to the target gait cycle includes:

dynamically updating a sliding factor value according to the target gait cycle to obtain a target sliding factor value, wherein the target sliding factor value is related to a user motion state in the target gait cycle, wherein the dynamically updating of the sliding factor value according to the target gait cycle to obtain the target sliding factor value includes:

dynamically updating, based on a time interval between a first candidate lift-off moment and a second candidate lift-off moment in the target gait cycle, the sliding factor value to obtain the target sliding factor value, wherein the target sliding factor value is negatively correlated to the time interval, and determining a lift-off time range in the target gait cycle and determining the target lift-off moment based on the target sliding factor value and the lift-off time range; and determining a gait feature of the target user based on at least the target lift-off moments corresponding to the M gait cycles.

16. The method according to claim 15, wherein the dynamically updating of the sliding factor value according to the target gait cycle to obtain the target sliding factor value includes:

dynamically updating the sliding factor value based on a motion speed of the target user in the target gait cycle to obtain the target sliding factor value, wherein the target sliding factor value is negatively correlated to the motion speed.

17. The method according to claim 15, wherein the gait data includes angular velocity data around a y-axis perpendicular to a direction the target user is facing; and the determining of the lift-off time range in the target gait cycle includes:

determining a moment corresponding to a target trough of the angular velocity data in the target gait cycle as a starting moment of the lift-off time range, and a moment corresponding to a target peak of the angular velocity data in the target gait cycle as an ending moment of the lift-off time range, wherein the target trough and the target peak are both located after a ground contact moment of the foot of the target user in the target gait cycle.

18. The method according to claim 17, wherein the determining of the target lift-off moment based on the target sliding factor value and the lift-off time range includes:

determining a difference between an angular velocity corresponding to the ending moment and an angular velocity corresponding to the starting moment, determining a target angular velocity based on the target sliding factor value and the difference, and searching for the target angular velocity in the lift-off time range, and determine a moment corresponding to the target angular velocity as the target lift-off moment; or determining a difference between an angular velocity corresponding to the ending moment and an angular velocity corresponding to the starting moment, determining a target angular velocity based on the target sliding factor value and the difference, searching for the target angular velocity in the lift-off time range, and determine a moment corresponding to the target angular velocity as a third candidate lift-off moment, and determining the target lift-off moment based on the first candidate lift-off moment, the second candidate lift-off moment and the third candidate lift-off moment in the target gait cycle.

* * * * *